United States Patent [19]

Bodor et al.

[11] 4,221,787
[45] Sep. 9, 1980

[54] ESTERAMIDE PRODRUGS OF ANTI-INFLAMMATORY CORTICOSTEROIDS

[75] Inventors: Nicholas S. Bodor, Gainesville, Fla.; Kenneth B. Sloan, Eudora, Kans.

[73] Assignee: INTERx Research Corporation, Lawrence, Kans.

[21] Appl. No.: 59,380

[22] Filed: Jul. 20, 1979

Related U.S. Application Data

[63] Continuation-in-part of Ser. No. 891,050, Mar. 28, 1978, abandoned.

[30] Foreign Application Priority Data

Mar. 28. 1979 [AU] Australia ............ 45483/79

[51] Int. Cl.$^2$ .......................... C07J 17/00; C07J 5/00; A61K 31/58

[52] U.S. Cl. .................. 424/241; 260/239.5

[58] Field of Search ............... 424/241; 260/239.5, 260/239.55 D, 397.45, 239.5 R

[56] References Cited

U.S. PATENT DOCUMENTS

| | | | |
|---|---|---|---|
| 3,562,255 | 2/1971 | Oliver et al. | 260/239.5 |
| 3,621,014 | 11/1971 | Stacke et al. | 260/397.45 |
| 4,069,322 | 1/1978 | Bador et al. | 260/239.5 |

*Primary Examiner*—Elbert L. Roberts
*Attorney, Agent, or Firm*—Burns, Doane, Swecker & Mathis

[57] ABSTRACT

Transient, C-21 and/or C-17 esteramide prodrugs of the anti-inflammatory corticosteroids, prepared by esterification of hydroxy steroids, are disclosed.

86 Claims, No Drawings

ESTERAMIDE PRODRUGS OF ANTI-INFLAMMATORY CORTICOSTEROIDS

CROSS-REFERENCE TO RELATED APPLICATION

This application is a continuation-in-part of our earlier copending application, Ser. No. 891,050, filed Mar. 28, 1978, now abandoned assigned to the assignee hereof and hereby expressly incorporated by reference in its entirety and relied upon.

TECHNICAL FIELD OF THE INVENTION

The present invention relates to certain selected transient prodrug forms of conventional anti-inflammatory steroids [e.g., cortisone, hydrocortisone, prednisone, prednisolone, etc.] useful in alleviating inflammatory conditions in warm-blooded animals.

For purposes of this application, the term "prodrug" denotes a derivative of a known and proven prior art anti-inflammatory steroid compound [e.g., cortisone, hydrocortisone, prednisone, prednisolone, etc.], which derivative, when administered to a warm-blooded animal, "cleaves" in such a manner as to release the proven drug form at its target site or sites of activity.

The term "transient" denotes enzymatic and/or chemical hydrolytic "cleavage" of the compounds of the instant invention in a manner such that the proven drug form [the conventional anti-inflammatory steroid, e.g., cortisone, hydrocortisone, prednisone, prednisolone, etc.] is released, while the remaining "cleaved" moiety remains nontoxic and is metabolized in such a manner that nontoxic, metabolic products are produced.

Finally, the term "pharmaceutically acceptable acid addition salt" as used herein generally includes the nontoxic acid addition salts of selected compounds of formula [I], formed with nontoxic inorganic or organic acids. For example, the salts include those derived from inorganic acids such as hydrochloric, hydrobromic, sulfuric, sulfamic, phosphoric, nitric and the like; and the salts prepared from organic acids such as acetic, propionic, succinic, glycollic, stearic, lactic, malic, tartaric, citric, ascorbic, pamoic, maleic, hydroxymaleic, phenylacetic, glutamic, benzoic, salicylic, sulfanilic, fumaric, sulfonic, toluenesulfonic, and the like.

BACKGROUND OF THE PRIOR ART

Conventional anti-inflammatory steroids, such as cortisone, hydrocortisone, prednisone, prednisolone, etc., are high molecular weight steroidal compounds containing a number of hydrophilic functions, e.g., hydroxyl and keto functions. These compounds are characterised as having (1) extremely low water solubility, (2) extensive intermolecular hydrogen bonding due to the combination of hydrophilic functions, such as —OH and =O [as evidenced by their high melting point], and (3) high molecular weight.

All three points enumerated above contribute to the inefficient and slow penetrability of these conventional steroidal compounds through biological barriers, among which the most important are (i) the skin and (ii) the gastrointestinal wall.

It is recognized that in the case of the skin, the higher molecular weight anti-inflammatory steroids are absorbed primarily through the appendages and the hair follicles as opposed to the more efficient molecular intercellular absorption. See, M. Katz and B. J. Poulsen, "Absorption of Drugs through the Skin", [Handbook of Experimental Pharmacology, Vol. XXVII/I, Chapter 7, page 104, Springer Verlag, Berlin-Heidelberg-New York (1971).

It too is art recognized that (4) a serious side effect of certain of the known anti-inflammatory steroids is the decrease in thickness, or atrophy, of the skin at the site of application; (5) another adverse effect is a deleterious, systemic side effect on the thymus gland; and (6) in certain instances, with certain of the, e.g., hydrocortisone derivatives, the reduction of inflammation is inadequate.

In view of the foregoing, it is apparent that a serious need exists for a class of novel anti-inflammatory steroidal compounds which will overcome the aforementioned inefficiencies such that penetration of the same through biological barriers will be enhanced, such that less atrophy results, such that less effect on the thymus gland is evidenced, and such that inflammation is reduced to the comparable extent of the highly potent triamcinolone acetonide.

BRIEF SUMMARY OF THE INVENTION

It is one object of the present invention to provide prodrug forms of conventional anti-inflammatory steroids which possess the capability of efficiently penetrating the biological barriers of warm-blooded animals, and, especially, the skin and the gastrointestinal wall.

Another object is the provision of prodrugs of conventional anti-inflammatory steroids which cause less atrophy and systemically affect the thymus to a much lesser degree, but which, nonetheless, remain highly potent.

It is another object of the present invention to provide such prodrug forms of conventional anti-inflammatory compounds which, following administration, will "cleave" in such a manner as to enable the original parent steroidal moiety [e.g., cortisone, hydrocortisone, prednisone, prednisolone, etc.] to be released at its therapeutic site or sites of anti-inflammatory activity and to further permit the cleaved moiety(ies) unassociated with the parent steroidal moiety to be metabolized in a nontoxic fashion.

All the foregoing objects are achieved by topically or orally administering to a warm-blooded animal afflicted with inflammation, a therapeutically effective anti-inflammatory amount of a compound having the structural formula:

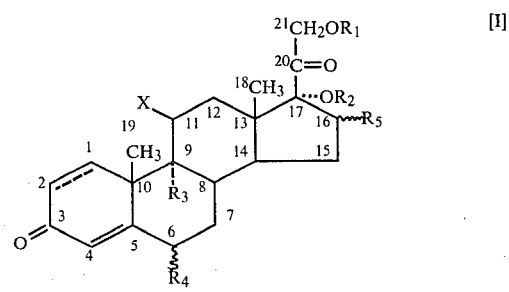

wherein $R_1$ and $R_2$, which can be the same or different, are each H,

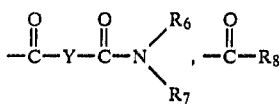

or

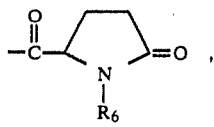

with the proviso that at least one of $R_1$ and $R_2$ is

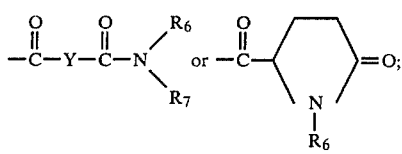

$R_3$ is H, F or Cl;
$R_4$ is H, $CH_3$, F or Cl;
$R_5$ is H, $CH_3$ or OH;
$R_6$ and $R_7$, which can be the same or different, are each H, $C_1$-$C_8$ alkyl or

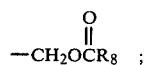

or $R_6$ and $R_7$, together with the nitrogen atom from which they both depend can form an N-heterocycle or N,O-heterocycle, (e.g., a 5- or 6-membered N-heterocycle or a 5- or 6-membered N,O-heterocycle, such as piperidine, morpholine, pyridine, piperazine, N-methylpiperazine, pyrrolidine, and the like);
$R_8$ is $C_1$-$C_{20}$ alkyl, $C_2$-$C_{20}$ alkenyl, $C_3$-$C_7$ cycloalkyl, phenyl, ($C_1$-$C_4$ alkyl substituted)phenyl or $C_1$-$C_{20}$ alkyl-$C_6$-$C_{10}$ aryl;
X is OH, e.g., β-OH, or =O;
Y is $-(CH_2)_n-$, wherein n ranges from 1 to 8, $-(CH_2)_n-Z-(CH_2)_m-$, wherein both n and m range from 1 to 8, $C_3$-$C_7$ cycloalkyl or phenyl;
Z is O or S; and
the dotted line indicates the optional presence of a 1,2-double bond.

Additionally, when $R_2$ is H and $R_5$ is OH, the corresponding cyclic ketal also is envisaged, e.g., acetonide (isopropylidenedioxy) or benzylidenedioxy. Further compare those cyclic ketal forming reactants, herein expressly incorporated by reference, in our U.S. Pat. No. 4,069,322 assigned to the assignee hereof.

DETAILED DESCRIPTION OF THE INVENTION

While all of the compounds encompassed within the above generic formula [I] essentially satisfy the objectives of the invention, nevertheless, certain selected compounds as are set forth immediately below, remain preferred:

[1] 4-Pregnene-11β,7α-dihydroxy-21-(N,N-dimethylsuccinamyloxy)-3,20-dione;
[2] 4-Pregene-11β,7α-dihydroxy-21-(N,N-diethylsuccinamyloxy)-3,20-dione;
[3] 4-Pregnene-11β,17α-dihydroxy-21-(N,N-dipropylsuccinamyloxy)-3,20-dione;
[4] 4-Pregnene-11β,17α-dihydroxy-21-(N,N-dibutylsuccinamyloxy)-3,20-dione;
[5] 4-Pregnene-11β,17α-dihydroxy-21-(N,N-dioctylsuccinamyloxy)-3,20-dione;
[6] 4-Pregnene-11β,17α-dihydroxy-21-(N,N-tetramethylenesuccinamyloxy)-3,20-dione;
[7] 4-Pregnene-11β,17α-dihydroxy-21-(N,N-pentamethylenesuccinamyloxy)-3,20-dione;
[8] 4-Pregnene-11β,17α-dihydroxy-21-[N,N-(3'-oxapentamethylene)succinamyloxy]-3,20-dione;
[9] 4-Pregnene-11β,17α-dihydroxy-21-[N,N-(N'-methyl-3'-azapentamethylene)succinamyloxy]-3,20-dione;
[10] 4-Pregnene-11β,17α-dihydroxy-21-(N,N-dibenzylsuccinamyloxy)-3,20-dione;
[11] 4-Pregnene-11β,7α-dihydroxy-21-(2'-oxopyrrolidin-5'-yl)carbonyloxy-3,20-dione;
[12] 4-Pregnene-11β-hydroxy-17α-acetyloxy-21-(N,N-diethylsuccinamyloxy)-3,20-dione;
[13] 4-Pregnene-11β-hydroxy-17α-butyryloxy-21-(N,N-diethylsuccinamyloxy)-3,20-dione;
[14] 4-Pregnene-11β-hydroxy-17α-valeryloxy-21-(N,N-diethylsuccinamyloxy)-3,20-dione;
[15] 4-Pregnene-11β,17α-dihydroxy-21-(N,N-diethylglutaramyloxy)-3,20-dione;
[16] 4-Pregnene-11β,17α-dihydroxy-21-(N,N-diethyladipamyloxy)-3,20-dione;
[17] 4-Pregnene-11β,17α-dihydroxy-21-(N,N-diethylsebacamyloxy)-3,20-dione;
[18] 4-Pregnene-11β,21-dihydroxy-17α-(N,N-dimethylsuccinamyloxy)-3,20-dione;
[19] 4-Pregnene-11β,21-dihydroxy-17α-(N,N-diethylsuccinamyloxy)-3,20-dione;
[20] 4-Pregnene-11β,21-dihydroxy-17α-(N,N-dipropylsuccinamyloxy)-3,20-dione;
[21] 4-Pregnene-11β,21-dihydroxy-17α-(N,N-dibutylsuccinamyloxy)-3,20-dione;
[22] 4-Pregnene-17α-hydroxy-21-(N,N-dioctylsuccinamyloxy)-3,11,20-trione;
[23] 4-Pregnene-17α-hydroxy-21-(N,N-tetramethylenesuccinamyloxy)-3,11,20-trione;
[24] 4-Pregnene-17α-hydroxy-21-(N,N-pentamethylenesuccinamyloxy)-3,11,20-trione;
[25] 1,4-Pregnadiene-11β,17α-dihydroxy-21-[N,N-3'-oxapentamethylene)succinamyloxy]-3,20-dione;
[26] 1,4-Pregnadiene-11β,17α-dihydroxy-21-[N,N-(N'-methyl-3'-azapentamethylene)succinamyloxy]-3,20-dione;
[27] 1,4-Pregnadiene-11β,17α-dihydroxy-21-(N,N-dibenzylsuccinamyloxy)-3,20-dione;
[28] 1,4-Pregnadiene-17α-hydroxy-21-(2'-oxopyrrolidin-5'-yl)carbonyloxy-3,11,20-trione;
[29] 1,4-Pregnadiene-17α-acetyloxy-21-(N,N-diethylsuccinamyloxy)-3,11,20-trione;
[30] 1,4-Pregnadiene-17α-butyryloxy-21-(N,N-diethylsuccinamyloxy)-3,11,20-trione;
[31] 1,4-Pregnadiene-9α-fluoro-11β,16α-dihydroxy-17α-valeryloxy-21-(N,N-diethylsuccinamyloxy)-3,20-dione;
[32] 1,4-Pregnadiene-9α-fluoro-11β,16α,17α-trihydroxy-21-(N,N-diethylglutaramyloxy)-3,20-dione;
[33] 1,4-Pregnadiene-9α-fluoro-11β,16α,17α-trihydroxy-21-(N,N-diethyladipamyloxy)-3,20-dione;
[34] 1,4-Pregnadiene-9α-fluoro-11β-hydroxy-16α,17α-isopropylidenedioxy-21-(N,N-dimethylsuccinamyloxy)-3,20-dione;

[35] 1,4-Pregnadiene-9α-fluoro-11β-hydroxy-16,α,17α-isopropylidenedioxy-21-(N,N-diethylsuccinamyloxy)-3,20-dione;

[36] 1,4-Pregnadiene-9α-fluoro-11β-hydroxy-16α,17α-isopropylidenedioxy-21-(N,N-dipropylsuccinamyloxy)-3,20-dione;

[37] 1,4-Pregnadiene-9α-fluoro-11β,17α-dihydroxy-16α-methyl-21-(N,N-diethylsebacamyloxy)-3,20-dione;

[38] 1,4-Pregnadiene-9α-fluoro-11β,21-dihydroxy-16α-methyl-17α-(N,N-dimethylsuccinamyloxy)-3,20-dione;

[39] 1,4-Pregnadiene-9α-fluoro-11β,21-dihydroxy-16α-methyl-17α-(N,N-diethylsuccinamyloxy)-3,20-dione;

[40] 4-Pregnene-9α-fluoro-11β,21-dihydroxy-17α-(N,N-dipropylsuccinamyloxy)-3,20-dione;

[41] 4-Pregnene-9α-fluoro-11β,21-dihydroxy-17α-(N,N-dibutylsuccinamyloxy)-3,20-dione;

[42] 4-Pregnene-9α-fluoro-11β,17α-dihydroxy-21-(N,N-dibutylsuccinamyloxy)-3,20-dione;

[43] 1,4-Pregnadiene-11β-hydroxy-16α,17α-isopropylidenedioxy-21-(N,N-dioctylsuccinamyloxy)-3,20-dione;

[44] 1,4-Pregnadiene-11β-hydroxy-16α,17α-isopropylidenedioxy-21-(N,N-tetramethylenesuccinamyloxy)-3,20-dione;

[45] 1,4-Pregnadiene-11β-hydroxy-16α,17α-isopropylidenedioxy-21-(N,N-pentamethylenesuccinamyloxy)-3,20-dione;

[46] 1,4-Pregnadiene-6α,9α-difluoro-16α-methyl-11β,17α-dihydroxy-21-[N,N-(3'-oxapentamethylene)succinamyloxy]-3,20-dione;

[47] 1,4-Pregnadiene-6α,9α-difluoro-16α-methyl-11β,17α-dihydroxy-21-[N,N-(N'-methyl-3'-azapentamethylene)-succinamyloxy]-3,20-dione;

[48] 1,4-Pregnadiene-6α,9α-difluoro-16α-methyl-11β,17α-dihydroxy-21-(N,N-dibenzylsuccinamyloxy)-3,20-dione;

[49] 1,4-Pregnadiene-6α,9α-difluoro-11β-hydroxy-16α,17α-isopropylidenedioxy-21-(2'-oxopyrrolidin-5'-yl)carbonyloxy-3,20-dione;

[50] 1,4-Pregnadiene-6α,9α-difluoro-11β-hydroxy-16α,17α-isopropylidenedioxy-21-(N,N-diethylglutaramyloxy)-3,20-dione;

[51] 1,4-Pregnadiene-6α,9α-difluoro-11β-hydroxy-16α,17α-isopropylidenedioxy-21-(N,N-diethyladipamyloxy)-3,20-dione;

[52] 1,4-Pregnadiene-9α-fluoro-11β-hydroxy-16α-methyl-17α-acetyloxy-21-(N,N-diethylsuccinamyloxy)-3,20-dione;

[53] 1,4-Pregnadiene-9α-fluoro-11α-hydroxy-16β-methyl-17α-acetyloxy-21-(N,N-diethylsuccinamyloxy)-3,20-dione;

[54] 1,4-Pregnadiene-9α-fluoro-11β-hydroxy-16α-methyl-17α-butyryloxy-21-(N,N-diethylsuccinamyloxy)-3,20-dione;

[55] 4-Pregnene-11β,21-dihydroxy-17α-[N,N-(N'-methyl-3'-azapentamethylene)succinamyloxy]-3,20-dione;

[56] 4-Pregnene-11β-hydroxy-17α,21-bis(N,N-diethylsuccinamyloxy)-3,20-dione; and

[57] 4-Pregnene-11β-hydroxy-21-(N,N-diethylsuccinamyloxy)-17α-[N,N-(N'-methyl-3'-azapentamethylene)-succinamyloxy-3,20-dione.

A preferred group of compounds of the present invention consists of the compounds of formula [I] wherein at least one of $R_1$ and $R_2$ is

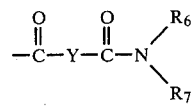

or

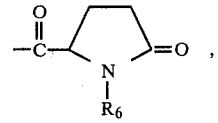

wherein Y, $R_6$ and $R_7$ are defined as hereinabove, and the remainder of the structural variables are identical to those found in one of the following known anti-inflammatory steroids: cortisone, hydrocortisone, hydrocortisone 17-butyrate, hydrocortisone 17-valerate, triamcinolone, triamcinolone acetonide, prednisone, prednisolone, methyl prednisolone, paramethasone, meprednisone, fluocinolone acetonide, fluprednisolone, flumethasone, dexamethasone, desonide, chloroprednisone, betamethasone, amcinafide, amcinafal, and flurandrenolone acetonide. Compounds of formula [I] wherein $R_1$ is

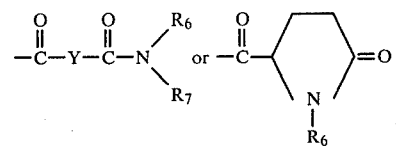

are especially preferred, particularly when the remaining structural variations correspond to those of the aforementioned known anti-inflammatory agents, and most especially when $R_2$ is H and $R_5$ is H or OH, or when $OR_2$ and $R_5$ together form a cyclic ketal such as the acetonide structure.

The compounds of the present invention can be prepared by known methods. Thus, the compounds of formula [I] wherein $R_1$ is

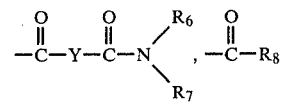

or

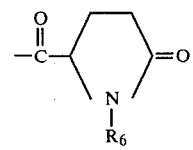

can be conveniently prepared by esterification of the corresponding 21-hydroxy steroids. The steroidal alcohol is contacted with the appropriate acid of the formula

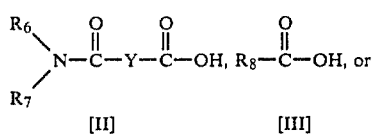 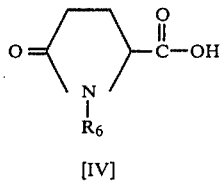

in the presence of a suitable dehydrating agent (e.g. dicyclohexylcarbodiimide). Alternatively, the acid chloride or acid anhydride corresponding to the acid of formula [II], [III] or [IV] can be reacted with the steroidal alcohol.

When the steroidal starting material employed in the procedure described above is a 17α,21-dihydroxy compound, the resultant 17α-hydroxy, 21-ester can be treated with cuprous iodide, methyl lithium and N,N,N',N'-tetramethylenediamine tetrachlorocuprate according to the procedure of G. H. Phillips, B. M. Bain and G. Durrant as described in U.S. Pat. No. 3,891,631 [*Chem. Abstr.*, 81, 4142 (1974)], to effect transfer of the ester group from the 21- to the 17-position, affording the corresponding 21-hydroxy, 17α-ester. That product can then be subjected to the hereinabove-described esterification process once again, to afford the 17α,21-diesters wherein the ester groups can be the same or different.

In order to still further illustrate the invention and the advantages thereof, the following specific examples are given, it being understood that same are intended only as illustrative and in nowise limitative.

EXAMPLE 1

Illustrative Preparation of Starting Materials

[a] N,N-Diethyl-3-oxaglutaramic acid

To a suspension of diglycolic dianhydride (11.02 g, 0.095 mole) in 50 ml dichloromethane was added dropwise, with cooling so that a temperature was maintained between 22°–25° C., diethylamine (7.13 g, 0.0975 mole). The reaction was then stirred at room temperature 1 hour. The light yellow solution was concentrated in vacuo to an oil which, after an unsuccessful crystallization attempt, was reconcentrated under strong vacuum to give 13 g (79% yield) of the desired compound as a light golden oil. NMR (CDCl$_3$) δ13.57

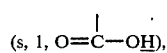

4.43

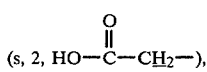

3.35 (m, 4, —N(CH$_2$CH$_3$)$_2$), 1.14 (m, 6, —N(CH$_2$CH$_3$)$_2$); IR (Neat) ~1730 cm$^{-1}$ (s, HO—C=O), 1620 cm$^{-1}$ (s, >N—C=O).

The remaining amides were prepared in a similar fashion to give the following compounds:

[b] N,N-(N'-Methyl-3'-azapentamethylene)succinamic acid

Analytical sample of yellow crystals from THF-Et$_2$O; mp 122°–127° C.; NMR (D$_2$O) δ3.87 (s, 4, O=C—N CH$_2$—), 3.33 (s, 4, CH$_3$—N CH$_2$), 2.90 (s, 3, >NCH$_3$), 2.57 (m,

IR (KBr) 1630 cm$^{-1}$

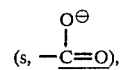

1600 cm$^{-1}$ (s, >N—C=O);

Anal. Calcd for C$_9$H$_{16}$N$_2$O$_3$: C, 53.98; H, 8.05; N, 13.99. Found: C, 53.72; H, 8.08; N, 13.78.

[c] N,N-(3'-Oxapentamethylene)succinamic acid

Analytical sample of clear, colorless crystals from THF-Et$_2$O; mp 73°–78° C.; NMR (D$_2$O) δ3.67 (s, 8, N—CH$_2$CH$_2$—O), 2.68

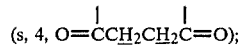

IR (KBr) 1730 cm$^{-1}$

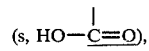

1605 cm$^{-1}$

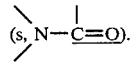

Anal. Calcd for C$_8$H$_{13}$NO$_4$: C, 51.32; H, 7.00; N, 7.48. Found: C, 51.54; H, 7.12; N, 7.35.

[d] N,N-Dipropylsuccinamic acid

Analytical sample of clear, colorless crystals from CH$_2$Cl$_2$; mp 35°–37° C.; NMR (CDCl$_3$) δ11.51 (m, 1, —OH), 3.28 (t, 4, NCH$_2$), 2.65 (s, 4, OC(CH$_2$)$_2$CO), 1.62 (m, 4, NCH$_2$CH$_2$), 0.94 (m, 6, N(CH$_2$CH$_2$CH$_3$)$_2$); IR (NaCl) 1725 cm$^{-1}$ (s) (O—C=O); 1630 cm$^{-1}$ and 1600 cm$^{-1}$ (s) (N—C=O).

Anal. Calcd for C$_{10}$H$_{19}$NO$_3$: C, 59.67; H, 9.52; N, 6.96. Found: C, 59.42; H, 9.59; N, 6.97.

[e] N,N-Tetramethylenesuccinamic acid

Yellow crystals mp 103°–108° C. from CH$_2$Cl$_2$-ether (75:200) in 87% yield; NMR (CDCl$_3$) δ11.8-11.1 (m, 1, OH), 3.7-3.3 (m, 4, CH$_2$—N), 2.63 (s, 4, O=C—CH$_2$CH$_2$C=O) and 2.25-1.6 (m, 4, CH$_2$—CH$_2$N).

Anal. Calcd for C$_8$H$_{13}$NO$_3$: C, 56.12; H, 7.65; N, 8.18. Found: C, 55.88; H, 7.52; N, 8.05.

[f] N,N-Diethylsuccinamic acid

Yellow crystals mp 80.5°–86° C. from CH$_2$Cl$_2$-heptane in 88% yield; NMR (CDCl$_3$) δ10.9-10.1 (m, s, O$\underline{H}$), 3.6-3.1 (m, 4, N—C$\underline{H}_2$CH$_3$), 2.67 (s, 4, O=C—C$\underline{H}_2$—C$\underline{H}_2$C=O) and 1.5-0.9 (m, 6, C$\underline{H}_3$—CH$_2$N).

Anal. Calcd for C$_8$H$_{15}$NO$_3$: C, 55.47; H, 8.73; N, 8.09. Found: C, 55.62; H, 8.83; N, 8.03.

The crude products above were used in subsequent reactions. Small amounts of material were recrystallized for the analytical data.

[g] N,N-Dimethylsuccinamic acid

N,N-dimethylsuccinamic acid was prepared in a somewhat different manner than the other amides. Since 40% dimethylamine in water was used as the amine source, the water had to be removed by evaporation at 60° C. (0.1 mm). The oily residue that remained was dissolved in CH$_2$Cl$_2$ and the CH$_2$Cl$_2$ solution was dried over Na$_2$SO$_4$. The CH$_2$Cl$_2$ solution (135 ml) was diluted first with 75 ml of ether, which caused an oil to form. The precipitate (4.1 g, mp 137°-147° C.) was not the desired compound (NMR) and was discarded. The filtrate was concentrated in vacuo to give a white solid (16.7 g) which was crystallized from hot THF to give the desired compound: 11.7 g, 47% yield; mp 86°-89°; NMR (CDCl$_3$) δ11.3 (s, 1, O$\underline{H}$), 3.05 and 2.96 (two s, 6, C$\underline{H}_3$—N) and 2.67 (s, 4, O=C—C$\underline{H}_2$CH$_2$—C=O).

Anal. Calcd. for C$_6$H$_{11}$NO$_3$: C, 49.64; H, 7.64; N, 9.65. Found: C, 50.00; H, 7.83; N, 9.70.

EXAMPLE 2

Preparation of 4-Pregnene-11β,17α-dihydroxy-21-(N,N-diethylsuccinamyloxy)-3,20-dione Hydrocortisone (14.6 g, 0.04 mole) was added to 50 ml of pyridine to give a clear yellow solution. Immediately, 6.92 g (0.04 mole) of N,N-diethylsuccinamic acid and 8.30 g (0.04 mole) of dicyclohexylcarbodiimide were added to the solution. As the clear solution became thick with precipitate, CH$_2$Cl$_2$ (100 ml) was added. The suspension was stirred overnight at room temperature. The suspension was then filtered and the filtrate was concentrated in vacuo to give a gum. The gum was triturated with 100 ml of THF. The resulting suspension was filtered and the filtrate was concentrated again. The residue from the concentration was then crystallized from THF-ether (50:25) initially but every hour or so an additional 100 ml of ether was added. The crystals that formed were filtered and dried to give 16.5 g of the desired compound as its etherate. A subsequent recrystallization from THF-ether as above gave 13.2 g (mp 100°-105° C., 64% yield) of the succinamate ester: TLC (silica gel, acetone) R$_f$0.37; IR (KBr) 3500-3400 cm$^{-1}$ (m) (OH) and 1735, 1715, 1645 and 1620 cm$^{-1}$ (s) (C=O); NMR (CDCl$_3$) δ5.65 (s, 1, O=C—C$\underline{H}$=C), 4.93 (s, 2, O=C—C$\underline{H}_2$—OC=O), 4.6-4.3 (m, 1, C$\underline{H}$—OH), 3.33 (q, J=7 Hz, 4, NC$\underline{H}_2$CH$_3$), 2.7 (m, 4, O=CC$\underline{H}_2$—C$\underline{H}_2$—C=O), 1.18 (t, J=7 Hz, 6, NCH$_2$C$\underline{H}_3$), 1.45 (s, 3, C$\underline{H}_3$—C), 0.97 (s, 3, C$\underline{H}_3$—C) and 3.1-0.8 (m, 23, C$\underline{H}_2$ and C$\underline{H}$ and 2, O$\underline{H}$); [α]$^{23.5}$ D+139° (C=0.55, ethanol).

Anal. Calcd for C$_{29}$H$_{43}$NO$_7$: C, 67.28; H, 8.56; N, 2.70. Found: C, 67.55; H, 8.75; N, 2.65.

EXAMPLE 3

Preparation of 4-Pregnene-11β,17α-dihydroxy-21-(N,N-dimethylsuccinamyloxy)-3,20-dione To 3.62 g (0.01 mole) of hydrocortisone dissolved in pyridine (14 ml) was quickly added 1.45 g (0.01 mole) of N,N-dimethylsuccinamic acid and 2.10 g (0.01 mole) of dicyclohexylcarbodiimide. The thick precipitate that formed was diluted with 28 ml of CH$_2$Cl$_2$ and the suspension was allowed to stir overnight at room temperature. The dicyclohexylurea was filtered and the filtrate was concentrated to give a pale greenish solid which was redissolved in CH$_2$Cl$_2$; that suspension was filtered. The CH$_2$Cl$_2$ filtrate was concentrated in vacuo to give a foam. The foam was crystallized from THF-ether to give 3.12 g of crystals which contained hydrocortisone by TLC. The crystals were recrystallized from THF (10 ml) to give 1.73 g (35% yield) of the desired product in analytically pure form; mp 228°-233° C.; TLC (silica gel, ether-methanol, 10:3), R$_f$0.5, IR (KBr) 3420 cm$^{-1}$ (s) (OH) 1735, 1720, 1655 and 1630 cm$^{-1}$ (s) (C=O); NMR (CDCl$_3$) δ 5.7 (s, 1, O=C—C$\underline{H}$=C), 4.97 (s, 2, O=C—C$\underline{H}_2$O$_2$C), 4.55-4.35 (m, 1, C$\underline{H}$—OH), 3.2 and 3.1 (two s, 6, N—C$\underline{H}_3$), 2.7 (m, 4, O—CC$\underline{H}_2$C$\underline{H}_2$C=O), 1.45 (s, 3, C$\underline{H}_3$—C), 0.97(s, 3, C$\underline{H}_3$—C) and 3.2-0.7 (m, 23, C$\underline{H}_2$ and C$\underline{H}$ and 2, O$\underline{H}$); [α]$^{25}$ D+137° (C=0.5, dioxane).

Anal. Calcd C$_{27}$H$_{39}$NO$_7$: C, 66.23; H, 8.03; N, 2.86. Found: C, 66.41; H, 8.35; N, 2.68.

EXAMPLE 4

Preparation of 4-Pregnene-11β,17α-dihydroxy-21-(N,N-tetramethylenesuccinamyloxy)-3,20-dione To 3.62 g (0.01 mole) of hydrocortisone dissolved in pyridine (14 ml) was quickly added 1.71 g (0.01) mole of N,N-tetramethylenesuccinamic acid and 2.10 g (0.01 mole) of dicyclohexylcarbodiimide. The thick precipitate that formed was diluted with 28 ml of CH$_2$Cl$_2$ and the suspension was allowed to stir overnight at room temperature. The dicyclohexylurea was filtered and the filtrate was concentrated in vacuo to give a green gum. The gum was suspended in CH$_2$Cl$_2$ (60 ml) and the suspension was filtered to give 2.5 g of an off-white solid. The white solid contained hydrocortisone by TLC. The solid was crystallized from 20 ml of boiling THF to give 1.94 g (mp 148°-154° C., 37% yield) of the desired ester as white crystals which were one spot upon TLC (silica gel, ether-methanol 10:3) R$_f$0.53. An analytically pure sample was obtained by further crystallization from THF: mp 152°-155° C.; IR (KBr) broad band from 3500-3300 cm$^{-1}$ (s) (OH) and 1720, 1700, 1660 and 1610 cm$^{-1}$, (s) (C=O); NMR (CDCl$_3$) δ 5.63 (s, 1, O=C—C$\underline{H}$=C), 4.93 (s, 2, O=C—C$\underline{H}_2$O$_2$C), 4.55-4.35 (m, 1, C$\underline{H}$—OH) 3.5-3.2 (m, 4, C$\underline{H}_2$N), 2.7-2.55 (m, 4, O=C—C$\underline{H}_2$C$\underline{H}_2$—C=O), 1.43 (s, 3, C$\underline{H}_3$—C), 0.93 (s, 3, C$\underline{H}_3$—C) and 3.1-0.8 (m, 27, C$\underline{H}_2$ and C$\underline{H}$ and 2, OH); [α]$^{25}$ D+116 (C=0.47, dioxane).

Anal. Calcd for C$_{29}$H$_{41}$NO$_7$·1.5 H$_2$O: C, 64.18; H, 8.17; N, 2.58. Found: C, 62.24; H, 7.94; N, 2.21.

EXAMPLE 5

Preparation of 4-Pregnene-11β,17α-dihydroxy-21-[N,N-(3'-oxapentamethylene)succinamyloxy]-3,20-dione To a solution of hydrocortisone (10 g, 0.028 mole) and N,N-(3'-oxapentamethylene)succinamic acid (5.16 g, 0.028 mole) in 50 ml pyridine was added dicyclohexylcarbodiimide (5.67 g, 0.028 mole). After the reaction was stirred 10 minutes, 50 ml CH$_2$Cl$_2$ was added to it to keep the suspension, which had formed, sufficiently fluid for stirring. The reaction was stirred overnight then filtered to give a residue of dicyclohexylurea which weighed 4.51 g (83% yield) and a filtrate which was concentrated in vacuo to a light off-white foam. The foam was in turn triturated (25 ml CH$_2$Cl$_2$, 3 hours) then filtered to give a residue weighing 6.4 g and a filtrate which was concentrated in vacuo to 10.4 g. The 10.4 g was in turn triturated (100 ml MeOH, overnight) then filtered to give a residue weighing 4.3 g. The residue was recrystallized from 200 ml EtOH to give a fine white crystalline product, which, after it was dried in vacuo (35° C., 2 hours), weighed 3.4 g: mp 223°–225° C.; NMR (DMSO-d$_6$) δ5.55 (s, 1, O=C—C$\underline{H}$=), 5.33 (s, 1, O$\underline{H}$), 4.93 (ABq, 2, J$_{AB}$=19 Hz, Δ$\nu_{AB}$=19 Hz, O=C—C$\underline{H}_2$—O), 4.28 (m, 2, C$\underline{H}$O$\underline{H}$), 3.50 (m, 8, N(C$\underline{H}_2$CH$_2$)$_2$O), 2.62 (s, 4, OCC$\underline{H}_2$C$\underline{H}_2$CO), 1.38 (s, 3, C—C$\underline{H}_3$), 0.78 (s, 3, C—C$\underline{H}_3$), 2.9–0.8 (m, 17, C$\underline{H}$, C$\underline{H}_2$-; IR (KBr) 3500–3300 cm$^{-1}$ (s) (OH), 1710, 1660 and 1610 cm$^{-1}$ (s) (C=O); [α]$^{25}$ D=+131, (C=0.5, dioxane); TLC (silica gel), 10% MeOH/Et$_2$O) R$_f$0.29.

Anal. Calcd for C$_{29}$H$_{41}$NO$_8$: C, 65.51; H, 7.77; N, 2.64. Found: C, 65.46; H, 7.99; N, 2.21.

EXAMPLE 6

Preparation of 4-Pregnene-11β,17α-dihydroxy-21-(N,N-diethyl-3'-oxaglutaramyloxy)-3,20-dione To a solution of hydrocortisone (5.12 g, 0.014 mole) and N,N-diethyl-3-oxaglutaramic acid (2.57 g, 0.015 mole) in 15 ml pyridine was added dicyclohexylcarbodiimide (3.06 g, 0.015 mole). After the reaction was stirred 10 minutes, 25 ml CH$_2$CH$_2$ was added to it to keep the suspension which had formed sufficiently fluid for stirring. The reaction was stirred overnight at room temperature then filtered. The residue was washed twice with CH$_2$Cl$_2$ and dried to give 2.6 g (89% yield) dicyclohexylurea. The filtrate was concentrated in vacuo to give a foam which was suspended in 20 ml hot dichloromethane and allowed to cool. The suspension was filtered and the filtrate was concentrated in vacuo to give a residue which was dissolved in 20 ml THF; the solution was then diluted to 100 ml with Et$_2$O. Crystals formed overnight and were filtered to give 2.69 g of product which TLC showed to be contaminated with hydrocortisone. These crystals were in turn recrystallized from THF-Et$_2$O (20:80). After 5 days, 2.14 g (29% yield) of light brown needles were filtered which were the etherate of the desired product: mp 95°–97.5° C., NMR (CDCl$_3$) δ5.67 (s, 1, O=C—C$\underline{H}$=), 5.07 (s, 2, O=C—C$\underline{H}_2$O—C=O), 4.48 (m, 3, C$\underline{H}$O$\underline{H}$,—O$\underline{H}$), 4.35 (s, 2, —OCOC$\underline{H}_2$O—), 4.30 (s, 2, NCOC$\underline{H}_2$O—), 3.48 (q, 4, O(C$\underline{H}_2$CH$_3$)$_2$, $\underline{J}$=5 Hz), 3.34 (m, 4, N(C$\underline{H}_2$CH$_3$)$_2$), 1.44 (s, 3, C—C$\underline{H}_3$), 1.18 (t, 6, O(CH$_2$C$\underline{H}_3$)$_2$, $\underline{J}$=5 Hz), 0.93 (s, 3, C—C$\underline{H}_3$), 2.9–0.9 (m, 23, C$\underline{H}$, C$\underline{H}_2$); IR (KBr) 3400 cm$^{-1}$ (s) OH and 1730, 1710 and 1640 cm$^{-1}$ (s) (C=O); TLC (silica gel, 10% MeOH/Et$_2$O) R$_f$ 0.36; [α]$^{23}$ D=+117° (C=0.5, dioxane).

Anal. Calcd for C$_{29}$H$_{43}$NO$_8$·C$_4$H$_{10}$O: C, 65.21; H, 8.79; N, 2.30. Found: C, 65.15; H, 8.60; N, 2.06.

EXAMPLE 7

Preparation of 4-Pregnene-11β,17α-dihydroxy-21-(N,N-dipropylsuccinamyloxy)-3,20-dione To a solution of hydrocortisone (5 g, 0.014 mole) and N,N-di-n-propylsuccinamic acid (2.78 g, 0.014 mole) in 25 ml pyridine at room temperature was added dicyclohexylcarbodiimide (2.85 g, 0.014 mole). After the reaction was stirred 10 minutes, 25 ml dichloromethane was added to it to keep the suspension which had formed sufficiently fluid for stirring. After the reaction was stirred overnight, it was filtered. The residue was washed twice with CH$_2$Cl$_2$ and dried in the air to give 2.46 g (91% yield) dicyclohexylurea. The filtrate was concentrated in vacuo to a residue which was dissolved in 25 ml hot THF. After the THF solution was filtered while hot, the resulting filtrate was diluted to 150 ml with Et$_2$O. The product crystallized overnight and was filtered and dried to give 3.49 g of light brown crystals, which a preliminary NMR showed to be contaminated with solvent. The crystals were dried in vacuo (50° C., 2 hours) to give 2.81 g (37% yield) of the desired product: mp 157°–162° C.; NMR (CDCl$_3$) δ5.64 (s, 1, O=C—CH=), 4.98 (m, 2, O=C—C$\underline{H}_2$O), 4.46 (m, 1, C$\underline{H}$O$\underline{H}$), 3.8–4.2 (m, 2, O$\underline{H}$), 3.24 (t, 4, $\underline{J}$=7 Hz, N C$\underline{H}_2$), 2.70 (s, 4, OCC$\underline{H}_2$C$\underline{H}_2$CO), 1.46 (s, 3, C-C$\underline{H}_3$), 0.96 (s, 3, C-C$\underline{H}_3$), 0.94 (m, 6, N(CH$_2$CH$_2$C$\underline{H}_3$)$_2$), 2.9–0.8 (m, 21, C$\underline{H}$, C$\underline{H}_2$); TLC (silica gel, 10% MeOH/Et$_2$O) R$_f$0.56; [α]$^{25}$ D=+127° (C=0.5, dioxane); IR (KBr) 3400 cm$^{-1}$ (s) (OH), 1730, 1710, 1640 and 1610 cm$^{-1}$ (s) (C=O).

Anal. Calcd for C$_{31}$H$_{47}$NO$_7$: C, 68.23; H, 8.68; N, 2.57. Found: C, 68.48; H, 9.02; N, 2.13.

EXAMPLE 8

Preparation of 4-Pregnene-11β,17α-dihydroxy-21-[N,N-(N'-methyl-3'-azapentamethylene)succinamyloxy]-3,20-dione To a solution of hydrocortisone (3.62 g, 0.01 mole) and N,N-(N'-methyl-3'-azapentamethylene)succinamic acid (2.00 g, 0.01 mole) in 15 ml pyridine at room temperature was added dicyclohexylcarbodiimide (2.00 g, 0.01 mole). After stirring the reaction mixture 10 minutes, 25 ml dichloromethane was added to it to keep the suspension, which had resulted, sufficiently fluid for stirring. After stirring overnight, the reaction was filtered. The residue was washed twice with CH$_2$Cl$_2$ and air dried to give 1.65 g (84% yield) dicyclohexylurea. The filtrate was concentrated in vacuo to give a light brown foam which was in turn triturated 2 hours with 10 ml CH$_2$Cl$_2$ to give a suspension which was filtered. The residue was dried in the vacuum oven 3 hours at 40° C. after a preliminary NMR showed contamination of the product with CH$_2$Cl$_2$. The resulting finely crystalline, off-white powder was the desired product: 2.70 g, 51% yield; mp 159°–163° C.; NMR (DMSO-d$_6$) δ5.53 (s, 1, O=C-C$\underline{H}$=C-), 5.32 (m, 1, C-O$\underline{H}$), 4.91 (ABq, 2, JAB=17 Hz, Δ$\nu_{AB}$=18 Hz, O=C-C$\underline{H}_2$-O), 4.29 (m, 2, CH-OH), 3.41 (m, 8, -N(C$\underline{H}_2$CH$_2$)N-), 2.59 (s, 3, N-C$\underline{H}_3$), 1.37 (s, 3, C-C$\underline{H}_3$), 0.78 (s, 3, C-C$\underline{H}_3$), 2.7–0.8 (m, 21, C$\underline{H}$, C$\underline{H}_2$); IR (KBr) 3400 cm$^{-1}$ (s) (OH), 1730 cm$^{-1}$ and 1710 cm$^{-1}$ (s) (C-C=O and O-C=O) and 1640 and 1615 cm$^{-1}$ (s) (O=C-CH=C, N-C=O); [α]$^{24}$ D=+122° (C=0.5, dioxane); TLC (silica gel, MeOH) R$_f$0.27.

Anal. Calcd for C$_{30}$H$_{44}$N$_2$O$_7$: C, 66.15; H, 8.14; N, 5.14. Found: C, 66.22; H, 8.21; N, 5.04.

EXAMPLE 9

Preparation of 4-Pregnene-11β-Hydroxy-17α-butyryloxy-21-(N,N-diethylsuccinamyloxy)-3,20-dione To 8.64 g (0.02 mole) of hydrocortisone 17-butyrate dissolved in 25 ml of pyridine was added a mixture of 4.4 g (0.021 mole) of dicyclohexylcarbodiimide and 3.46 g (0.02 mole) of N,N-diethylsuccinamic acid. After 4 minutes, 50 ml of dichloromethane was added to the clear solution. After 4 hours, the precipitate that had formed was filtered and washed with 100 ml of dichloromethane. The filtrate was concentrated in vacuo to gum which was chromatographed on Silic AR CC-7 (500 g) using ether as the eluent to give three fractions.

The first fraction was crystallized from methanol to give 272 mg (mp 180°–190° C., 3% yield) of hydrocortisone 21-butyrate.

The second fraction was crystallized from methanol to give 825 mg (mp 211°–214° C., 9.5% recovery) of hydrocortisone 17-butyrate.

The third fraction was crystallized from dichloromethaneheptane 60:360 to give 5.28 g (mp 81°–83°, 44% yield) of the desired hydrocortisone 17-butyrate 21-(N,N-diethylsuccinamate): TLC (silica gel, ether) developed twice, $R_f$ 0.25; IR (KBr) 3460–3360 cm$^{-1}$ (m) (OH) 1720 cm$^{-1}$ (s) (C=O) and 1640, 1630 and 1615 cm$^{-1}$ (s) (C=O); NMR (CDCl$_3$) $\delta$5.65 (s, 1, O=C-CH=C), 4.65 (AB quartet, 2, $\underline{J}$=14 Hz, $\Delta_{\nu AB}$=33 Hz, O-CH$_2$-C=O), 4.47 (broad m, 1, CH-OH), 3.30 (q, 4, $\underline{J}$=8 Hz, CH$_3$CH$_2$N), 2.60 (broad s, 4, O=C-CH$_2$CH$_2$C=O), 1.37 (s, 3, CH$_3$-C) and 3.0–0.7 (m, 33, CH$_3$, CH$_2$ and CH and 1, OH); $[\alpha]^{26.5°}$ D+67°, (C=0.5, dioxane).

Anal. Calcd for C$_{33}$H$_{49}$NO$_8$·0.5 H$_2$O; C, 66.41; H, 8.44; N, 2.34. Found: C, 66.76; H, 8.56; N, 2.00.

EXAMPLE 10

Preparation of 4-Pregnene-11β-hydroxy-17α-butyryloxy-21-(2'-oxopyrrolidin-5'-yl)carbonyloxy-3,20-dione A mixture of 2.16 g (0.005 mole) of hydrocortisone 17-butyrate, 0.65 g (0.005 mole) of L-2-pyrrolidone-5-carboxylic acid and 1.05 g (0.005 mole) of dicyclohexylcarbodiimide was partially dissolved in CH$_2$Cl$_2$ (50 ml) to which 1 ml of pyridine was added. The resulting suspension was allowed to react overnight. Then the dicyclohexylurea was filtered and the filtrate was concentrated in vacuo to a gum which was triturated with ether to remove some of the unreacted hydrocortisone 17-butyrate. The ether solution was adsorbed onto and chromatographed on silicAR CC-7 using first ether and then acetone to give two fractions. The first fraction that was eluted with ether was hydrocortisone 17-butyrate and it was discarded. The second acetone soluble fraction was the desired compound: 1.32 g, 49% yield; foamed at 85° C.; IR (KBr) 3420–3360 cm$^{-1}$ (m) (OH) and 1750–1650 cm$^{-1}$ (broad s) (C=O); NMR (CDCl$_3$) $\delta$6.83 (broad s, 1, N-H), 5.7 (s, 1, O=C-CH=C) 4.9 (AB quartet, $\underline{J}$=16 Hz, $\Delta_{\nu AB}$=18 Hz, 2, O=C-CH$_2$-O-C=O), 4.6–4.2 (m, 2, O$_2$C-CH-N and CH-OH), 1.45 (s, 3, CH$_3$-C), 1.0 (s, 3, CH$_3$-C) and 3.2–0.8 (m, 27, CH$_2$ and CH and 2, OH); $[\alpha]^{27}$ D+49° (C=0.5, dioxane).

Anal. Calcd for C$_{30}$H$_{41}$NO$_8$: C, 66.28; H, 7.60; N, 2.58. Found: C, 65.86; H, 7.70; N, 2.96.

EXAMPLE 11

Preparation of 4-Pregnene-11β,17α-dihydroxy-21-(2'-oxopyrrolidin-5'-yl)carbonyloxy-3,20-dione A mixture of 21.6 g (0.06 mole) of hydrocortisone, 7.8 g (0.06 mole) of L-2-pyrrolidone-5-carboxylic acid and 12.6 g (0.06 mole) of dicyclohexylcarbodiimide was dissolved in 40 ml of pyridine. A vigorous reaction resulted which caused the solution to solidify. The solid was suspended in 375 ml of CH$_2$Cl$_2$ overnight, then filtered. The filtrate was concentrated in vacuo to a foam which was redissolved in 50 ml of CH$_2$Cl$_2$ and filtered. The CH$_2$Cl$_2$ solution was diluted with 600 ml of ether. The gummy solid suspension that resulted gradually became a fine white powder after the suspension was stirred for 2 hours. The suspension was then filtered and dried in vacuo at 60° for 10 hours to give 22.1 g (mp 140°–142° C., 77% yield) of the desired compound: TLC (silica gel, acetone) $R_f$ 0.46; IR (KBr) 3400 cm$^{-1}$ (m) (broad OH and NH) and 1650 cm$^{-1}$ (s) (broad C=O); NMR (CDCl$_3$) $\delta$6.67 (s, 1, N-H), 5.63 (s, 1, O=C-CH=C), 5.03 (broad s, 2, O=C-CH$_2$-O), 4.6–4.3 (m, 2, CH-OH and O$_2$C-CH-N), 1.43 (s, 3, CH$_3$-CO), 0.90 (s, 3, CH$_3$-C) and 3.2–0.7 (m, 21, CH$_2$, CH, 2, OH); $[\alpha]^{27}$ C+131° (C=1.0, methanol).

Anal. Calcd for C$_{26}$H$_{35}$NO$_7$: C, 65.94; H, 7.45; N, 2.96. Found: C, 65.47; H, 7.54; N, 3.37.

EXAMPLE 12

Preparation of 1,4-Pregnadiene-17α-hydroxy-21-(N,N-diethylsuccinamyloxy)-3,11,20-trione To 3.58 g (0.01 mole) of prednisone partially dissolved in 10 ml of pyridine was added 1.73 g (0.01 mole) of N,N-diethylsuccinamic acid and 2.06 g (0.01 mole) of dicyclohexylcarbodiimide. After 1 hour, CH$_2$Cl$_2$ (10 ml) was added and after 3 hours, the suspension that resulted was filtered. The filtrate was concentrated in vacuo to give a foam which was dissolved in 15 ml of THF. The THF solution was filtered and warmed to boiling, then diluted with ether until the solution was nearly cloudy. The solution was allowed to cool overnight. The crystals were filtered to give 3.70 g (mp 186°–197° C., 72% yield) of the desired compound in a crude form. These crystals were purified by recrystallization from 10 ml of THF to give 2.40 g (mp 204°–206° C., 47% yield) of the pure ester: IR (KBr) 3400 cm$^{-1}$ (m) (OH) 1730, 1715, 1695, 1655, 1625 and 1613 cm$^{-1}$ (s) (C=O); NMR (CDCl$_3$) $\delta$6.95 (AX quartet, 2, $\underline{J}_{AX}$=10 Hz, $\Delta_{\nu AX}$=91 Hz, O=C-CH=CH), 6.07 (s, 1, O=C-CH=C), 4.90 (AB quartet, 2, $\underline{J}$=18 Hz, $\Delta_{\nu AB}$=21.5 Hz, O=C-CH$_2$-O), 4.67 (s, 1, OH), 1.47 (s, 3, CH$_3$-C), 0.67 (s, 3, CH$_3$-C) and 3.8–1.0 (m, 27, CH$_3$, CH$_2$ and CH); $[\alpha]^{24}$ D+144.5 (C=0.55, dioxane).

Anal. Calcd for C$_{29}$H$_{39}$NO$_7$: C, 67.81; H, 7.65; N, 2.73. Found: C, 68.15; H, 7.80; N, 2.40.

EXAMPLE 13

Preparation of 1,4-Pregnadiene-11β,17α-dihydroxy-9α-fluoro-16α-methyl-21-(N,N-diethylsuccinamyloxy)-3,20-dione To 3.90 g (0.01 mole) of 1,4-pregnadiene-11β,17α,21-trihydroxy-9α-fluoro-16α-methyl-3,20-dione (dexamethasone) dissolved in 10 ml of pyridine was added 1.73 g (0.01 mole) of N,N-diethylsuccinamic acid and 2.06 g (0.01 mole) of dicyclohexylcarbodiimide. The solution that resulted quickly became a thick suspension which was diluted with 10 ml of CH$_2$Cl$_2$. After 3 hours, the suspension was filtered and the filtrate was concentrated in vacuo to give a foam. The foam was dissolved in 30 ml of hot THF and filtered. The filtrate was diluted with ether until it nearly turned cloudy, then it was allowed to cool overnight. The crystals were filtered to give 3.68 g (mp 195°–226° C., 67% yield) of the crude product contaminated with dexamethasone. The crude product was recrystallized from THF (10 ml) to give 2.30 g (mp 202°–204° C., 42% yield) of the desired ester: IR (KBr) 3400 cm$^{-1}$ (m) (OH) and 1730, 1710, 1650 and 1610 cm$^{-1}$ (s) (C=O); NMR (CDCl$_3$) δ6.80 (AX quartet, 2, $J_{ax}$=10 Hz, $\Delta\nu_{AX}$=61 Hz, O=C-C<u>H</u>=C<u>H</u>), 6.1 (s, 1, O=C-C<u>H</u>=C), 4.93 (broad s, 1, O=C-C<u>H</u>$_2$-O), 4.55–4.1 (m, 1, C<u>H</u>-OH), 1.57 (s, 3, C<u>H</u>$_3$-C), 1.05 (s, 3, C<u>H</u>$_3$-C) and 3.9–0.8 (m, 34, C<u>H</u>$_3$, C<u>H</u>$_2$, C<u>H</u>, 2, O<u>H</u>); [α]$^{24}$ D+68° (C=0.5, dioxane).

Anal. Calcd for C$_{30}$H$_{42}$NO$_7$: C, 65.79; H, 7.73; N, 2.56. Found: C, 68.15; H, 7.80; N, 2.40.

EXAMPLE 14

Preparation of 4-Pregnene-11β,21-dihydroxy-17α-(N,N-diethylsuccinamyloxy)-3,20-dione To a suspension of 0.456 g (0.0024 mole) of cuprous iodide in 20 ml of dry THF at 0° C. was added 2.66 ml of 1.6 M methyl lithium (0.0043 mole) in ether. The reaction mixture was stirred at 0° C. for 15 minutes, then the temperature was reduced to −30° C. and 4-pregnene-11β,17α-dihydroxy-21-(N,N-diethylsuccinamyloxy)-3,20-dione (0.50 g, 0.00096 mole) was added. The reaction was stirred at −25° C. for 45 minutes then 1.53 g of N,N,N',N'-tetramethylenediamine tetrachlorocuprate was added and the reaction mixture was allowed to warm to room temperature. The mixture was stirred overnight at room temperature, then was poured into 150 ml of 3 M NH$_4$Cl and stirred for one hour. The oily precipitate was extracted with ethyl acetate and chromatographed on silicAR CC-7 using methanol-ether 10:90 as the eluent to give crystals (0.12 g, mp 160°–170° C., from methanol) of the desired product: IR (KBr) 3460 cm$^{-1}$ (s) (O-H), 1720, 1705 (sh), 1660, 1625 and 1610 (sh) cm$^{-1}$ (s) (C=O); NMR (CDCl$_3$) δ5.66 (m, 1, O=C-C<u>H</u>=C), 4.6–4.3 (m, 1, C<u>H</u>-OH), 4.27 (s, 2, O=CC<u>H</u>$_2$-OH), 3.5–3.1 (m, 4, NC<u>H</u>$_2$CH$_3$), 2.60 (sharp m, 4, O=CC<u>H</u>$_2$C<u>H</u>$_2$C=O), 1.61 (s, 3, C<u>H</u>$_3$-C), 0.95 (s, 3, C<u>H</u>$_3$-C), 1.17 (t, J=6 Hz, 6, N-CH$_2$C<u>H</u>$_3$), 3.0–0.8 (m, 19, CH$_2$, CH and OH).

Anal. Calcd for C$_{29}$H$_{43}$NO$_7$.H$_2$O: C, 65.02; H, 8.46; N, 2.61. Found: C, 64.96; H, 8.30; N, 2.58.

Substitution of an equivalent quantity of 4-pregnene-11β,17α-dihydroxy-21-[N,N-(N'-methyl-3'-azapentamethylene)succinamyloxy]-3,20-dione for the 4-pregnene-11β,17α-dihydroxy-21-(N,N-diethylsuccinamyloxy)-3,20-dione used above and substantial repetition of the foregoing procedure afforded 4-pregnene-11β,21-dihydroxy-17α-[N,N-(N'-methyl-3'-azapentamethylene)succinamyloxy]-3,20-dione.

EXAMPLE 15

The procedure of Example 9 was repeated, except that an equivalent quantity of 4-pregnene-11β,21-dihydroxy-17α-(N,N-diethylsuccinamyloxy)-3,20-dione was used in place of the hydrocortisone 17-butyrate. There was thus obtained 4-pregnene-11β-hydroxy-17α,21-bis(N,N-diethylsuccinamyloxy)-3,20-dione.

Similarly, use of an equivalent amount of 4-pregnene-11β,21-dihydroxy-17α-[N,N-(N'-methyl-3'-azapentamethylene)succinamyloxy]-3,20-dione as the steroidal starting material in the procedure of Example 9 afforded 4-pregnene-11β-hydroxy-21-(N,N-diethylsuccinamyloxy)-17α-[N,N-(N'-methyl-3'-azapentamethylene)-succinamyloxy]-3,20-dione.

EXAMPLE 16

Following those procedures and methods outlined in the foregoing Examples 1 to 15, but merely by substituting the appropriate specific reactants, the following additional compounds according to the invention are prepared: 4-pregnene-11β,17α-dihydroxy-21-(N,N-dibutylsuccinamyloxy)-3,20-dione; 4-pregnene-11β,17α-dihydroxy-21-(N,N-dioctylsuccinamyloxy)-3,20-dione; 4-pregnene-11β,17α-dihydroxy-21-(N,N-pentamethylenesuccinamyloxy)-3,20-dione; 4-pregnene-11β,17α-dihydroxy-21-(N,N-dibenzylsuccinamyloxy)-3,20-dione; 4-pregnene-11β-hydroxy-17α-acetyloxy-21-(N,N-diethylsuccinamyloxy)-3,20-dione; 4-pregnene-11β-hydroxy-17α-valeryloxy-21-(N,N-diethylsuccinamyloxy)-3,20-dione; 4-pregnene-11β,17α-dihydroxy-21-(N,N-diethylglutaramyloxy)-3,20-dione; 4-pregnene-11β,17α-dihydroxy-21-(N,N-diethyladipamyloxy)-3,20-dione; 4-pregnene-11β,17α-dihydroxy-21-(N,N-diethylsebacamyloxy)-3,20-dione; 4-pregnene-11β,21-dihydroxy-17α-(N,N-dimethylsuccinamyloxy)-3,20-dione; 4-pregnene-11β,21-dihydroxy-17α-(N,N-diethylsuccinamyloxy)-3,20-dione; 4-pregnene-11β,21-dihydroxy-17α-(N,N-dipropylsuccinamyloxy)-3,20-dione; 4-pregnene-11β,21-dihydroxy-17α-(N,N-dibutylsuccinamyloxy)-3,20-dione; 4-pregnene-17α-hydroxy-21-(N,N-dioctylsuccinamyloxy)-3,11,20-trione; 4-pregnene-17α-hydroxy-21-(N,N-tetramethylenesuccinamyloxy)-3,11,20-trione; 4-pregnene-17α-hydroxy-21-(N,N-pentamethylenesuccinamyloxy)-3,11,20-trione; 1,4-pregnadiene-11β,17α-dihydroxy-21-[N,N-(3'-oxapentamethylene)succinamyloxy]-3,20-dione; 1,4-pregnadiene-11β,17α-dihydroxy-21-[N,N-(N'-methyl-3'-azapentamethylene)-succinamyloxy]-3,20-dione; 1,4-pregnadiene-11β,17α-dihydroxy-21-(N,N-dibenzylsuccinamyloxy)-3,20-dione; 1,4-pregnadiene-17α-hydroxy-21-(2'-oxopyrrolidin-5'-yl)-carbonyloxy-3,11,20-trione; 1,4-pregnadiene-17α-acetyloxy-21-(N,N-diethylsuccinamyloxy)-3,11,20-trione; 1,4-pregnadiene-17α-butyryloxy-21-(N,N-diethylsuccinamyloxy)-3,11,20-trione; 1,4-pregnadiene-9α-fluoro-11β,16α-dihydroxy-17α-valeryloxy-21-(N,N-diethylsuccinamyloxy)-3,20-dione; 1,4-pregnadiene-9α-fluoro-11β,16α,17α-trihydroxy-21-(N,N-diethylglutaramyloxy)-3,20-dione; 1,4-pregnadiene-9α-fluoro-11β,16α,17α-trihydroxy-21-(N,N-diethyladipamyloxy)-3,20-dione; 1,4-pregnadiene-9α-fluoro-11β-hydroxy-16α,17α-isopropylidenedioxy-21-(N,N-dimethylsuccinamyloxy)-3,20-dione; 1,4-pregnadiene-9α-fluoro-11β-hydroxy-16α,17α-isopropylidenedioxy-21-(N,N-diethylsuccinamyloxy)-3,20-dione; 1,4-pregnadiene-9α-fluoro-11β-hydroxy-16α,17α-isopropylidenedioxy-21-(N,N-dipropylsuccinamyloxy)-3,20-dione; 1,4-pregnadiene-9α-fluoro-11β,17α-dihydroxy-16α-methyl-21-(N,N-diethylsebacamyloxy)-3,20-dione; 1,4-pregnadiene-9α-fluoro-11β,21-dihydroxy-16α-methyl-17α-(N,N-dimethylsuccinamyloxy)-3,20-dione; 1,4-pregnadiene-9α-fluoro-11β,21-dihydroxy-16α-methyl-17α-(N,N-diethylsuccinamyloxy)-3,20-dione; 4-pregnene-9α-fluoro-11β,21-dihydroxy-17α-(N,N-dipropylsuccinamyloxy)-3,20-dione; 4-pregnene-9α-fluoro-11β,21-dihydroxy-17α-(N,N-dibutylsuccinamyloxy)-3,20-dione; 4-pregnene-9α-fluoro-11β,17α-dihydroxy-21-(N,N-dibutylsuccinamyloxy)-3,20-dione; 1,4-pregnadiene-11β-hydroxy-16α,17α-isopropylidenedioxy-21-(N,N-dioctylsuccinamyloxy)-3,20-dione; 1,4-pregnadiene-11β-hydroxy-16α,17α-isopropylidenedioxy-21-(N,N-tetramethylenesuccinamyloxy)-3,20-dione; 1,4-pregnadiene-11β-hydroxy-16α,17α-isopropylidenedioxy-21-(N,N-pentamethylenesuccinamyloxy)-3,20-dione; 1,4-pregnadiene-6α,9α-difluoro-16α-methyl-11β,17α-dihydroxy-21-[N,N-(3'-oxapentamethylene)- succinamyloxy]-3,20-dione; 1,4-pregnadiene-6α,9α-difluoro-16α-methyl-11β,17α-dihydroxy-21-[N,N-(N'-methyl-3'-azapentamethylene)succinamyloxy]-3,20-dione; 1,4-pregnadiene-6α,9α-difluoro-16α-methyl-11β,17α-dihydroxy-21-(N,N-dibenzylsuccinamyloxy)-3,20-dione; 1,4-pregnadiene-6α,9α-difluoro-11β-hydroxy-16α,17α-isopropylidenedioxy-21-(2'-oxopyrrolidin-5'-yl)carbonyloxy-3,20-dione; 1,4-pregnadiene-6α,9α-difluoro-11β-hydroxy-16α,17α-isopropylidenedioxy-21-(N,N-diethylglutaramyloxy)-3,20-dione; 1,4-pregnadiene-6α,9α-difluoro-11β-hydroxy-16α,17α-isopropylidenedioxy-21-(N,N-diethyladipamyloxy)-3,20-dione; 1,4-pregnadiene-9α-fluoro-11β-hydroxy-16α-methyl-17α-acetyloxy-21-(N,N-diethylsuccinamyloxy)-3,20-dione; 1,4-pregnadiene-9α-fluoro-11α-hydroxy-16β-methyl-17α-acetyloxy-21-(N,N-diethylsuccinamyloxy)-3,20-dione; and 1,4-pregnadiene-9α-fluoro-11β-hydroxy-16α-methyl-17α-butyryloxy-21-(N,N-diethylsuccinamyloxy)-3,20-dione.

EXAMPLE 17

Effect of Selected Steroid Derivatives on Skin Thickness

A modification of the method of Smith et al, Arch Derrmatol, 112, 1115 (1976), was used. Hairless mice were used instead of rats. The steroids were tested at 0.03 M in propyleneglycol suspension except for hydrocortisone 17-butyrate which was soluble. Each suspension (50 μl) was applied to the backs of 9 mice daily. On the twenty-ninth day of the experiment, the mice were sacrificed with carbon dioxide and the double fold skin thickness was immediately measured using an Ames micrometer accurate to 0.0001 inch at a pressure of 28 lb/cm². The measurement was taken after three minutes had elapsed from the time the mouse skin was placed in the micrometer. The results are shown in Table I:

TABLE I

| | % Decrease from Control |
|---|---|
| Control (propylene glycol) | |
| Hydrocortisone 21-acetate | 37.5 |
| Hydrocortisone 21-(N,N-diethylsuccinamate) | 26.7 |
| Hydrocortisone 17-butyrate | 39.2 |
| Triamcinolone acetonide | 45.8 |

EXAMPLE 18

Effect of Selected Steroid Derivatives on Ear Burn Inflammation

A modification of the method of Tonelli et al, Endocrinology, 77, 625 (1965), was used. Sprague-Dawley rats were used which had a weight of 55±5 gm. The rats were first anesthetized with phenobarbitol, then the right ear of each rat was burned on both side for 10 seconds between two vertically oriented brass cylinders heated with water at 51.7° C. from a constant temperature bath. The pressure of the cylinder on the rat ear was reproduced by using only the weight of the top brass cylinder (2.5 lbs) to apply the pressure. The burned rat ear was then immediately treated on both sides with 50 ml of vehicle (isopropyl myristate) or 0.03 M steroid in the vehicle. After 16 hours, both ears of the rat were removed along anatomical guidelines and weighed.

The increase of weight caused by the burn was determined by subtracting the weight of the untreated left ear from the weight of the treated right ear.

The percent inhibition of inflammation was then determined as the weight increase of burned rat ears treated only with vehicle minus the weight increase of burned rat ears treated with vehicle containing the steroid divided by the weight increase of burned rat ears treated only with vehicle times one hundred. The results for 5 rats are shown in Table II:

TABLE II

| | % Inhibition |
|---|---|
| Hydrocortisone | 3.3 |
| Hydrocortisone 21-acetate | 31.0 |
| Hydrocortisone 21-(N,N-diethylsuccinamate) | 49.2 |
| Hydrocortisone 17-butyrate | 28.9 |
| Triamcinolone acetonide | 53.8 |
| Hydrocortisone 21-(2'-oxopyrrolidin-5'-yl)carboxylate | 50.5 |
| Hydrocortisone 21-(N,N-diethylsuccinamate) 17-butyrate | 20.4 |

EXAMPLE 19

Effect of Selected Steroid Derivatives on Thymus Weight

The rats used in the ear burn test described in Example 18 were revived and 48 hours after the burn and application of the steroid, they were sacrificed with carbon dioxide. Then their thymus glands were removed and weighed. The results are shown in Table III. The lower the weight of thymus, the more pronounced the systemic effect of the steroid. There was no significant difference in the relative toxicity of the steroids when the steroid was applied to unanesthetized rats which did not have their ears burned and removed.

TABLE III

| | Thymus Weight (mg) |
|---|---|
| Control | 233.5 ± 11.5 |
| Hydrocortisone | 190.3 ± 29.7 |
| Hydrocortisone 21-acetate | 177.2 ± 11.0 |
| Hydrocortisone 21-(N,N-diethylsuccinamate) | 215.7 ± 20.1 |
| Hydrocortisone 17-butyrate | 149.6 ± 11.7 |
| Triamcinolone acetonide | 65.3 ± 8.1 |
| Hydrocortisone 21-(2'-oxopyrrolidin-5'-yl)carboxylate | 151.9 ± 7.0 |
| Hydrocortisone 21-(N,N-diethylsuccinamate)17-butyrate | 176.8 ± 7.6 |

The compounds of the present invention are conveniently administered to warm-blooded animals via conventional oral or topical administration with any suitable nontoxic pharmaceutically acceptable oral or topical inert carrier material. Such carrier materials are well-known to those skilled in the art of oral and topical pharmaceutical formulations. For those not skilled in the art, reference is made to the text entitled REMINGTON'S PHARMACEUTICAL SCIENCES, (Fourteenth Edition), 1970. In a typical preparation for oral administration, e.g., tablet or capsule, any one of the compounds of the instant invention is combined in an anti-inflammatory effective amount with any oral nontoxic pharmaceutically acceptable inert carrier such as lactose, starch (pharmaceutical grade), dicalcium phosphate, calcium sulfate, kaolin, mannitol and powdered sugar. Additionally, when required, suitable binders, lubricants, disintegrating agents and coloring agents can also be included. Typical binders include starch, gelatin, sugars such as sucrose, molasses and lactose, natural and synthetic gums such as acacia, sodium alginate, extract of Irish moss, carboxymethylcellulose, methylcellulose, polyvinylpyrrolidone, polyethylene glycol, ethylcellulose and waxes. Typical lubricants for use in these dosage forms can include, without limitation, boric acid, sodium benzoate, sodium acetate, sodium chloride, leucine and polyethylene glycol. Suitable disintegrators can include, without limitation, starch, methylcellulose, agar, bentonite, cellulose, wood products, alginic acid, guar gum, citrus pulp, carboxymethylcellulose and sodium lauryl sulfate. If desired, a conventional pharmaceutically acceptable dye can be incorporated into the dosage unit form, i.e., any of the standard FD&C dyes.

Similarly, in a typical formulation for topical application, any one of the compounds of the instant invention is combined with triacetin, such that the active ingredient is present in an anti-inflammatory effective amount. The preparation is simply applied topically to the inflamed area, whereby the therapeutically active compound is dermally absorbed and "cleaved" to release the parent steroidal moiety at the site of inflammation.

Naturally, the therapeutic dosage range for the compounds of the instant invention will vary with the size and needs of the patient. However, generally speaking, the following dosage guidelines will suffice. On an oral basis, the therapeutic dose required for a compound of the instant invention will generally, on a molecular basis, mimic that for the parent conventional steroid moiety [e.g., cortisone, hydrocortisone, prednisone, prednisolone, etc.]. On a topical basis, application of a 0.01% to 2.5% concentration of a compound of the instant invention (in a suitable topical carrier material) to the site of inflammation should suffice.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A compound having the structural formula:

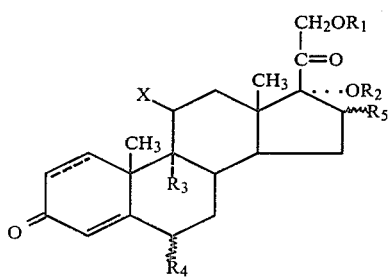

wherein $R_1$ and $R_2$, which can be the same or different, are each H,

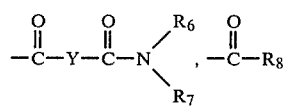

or

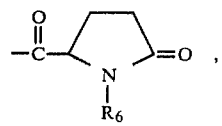

with the proviso that at least one of $R_1$ and $R_2$ is

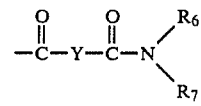

or

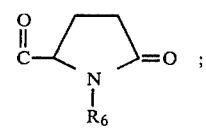

$R_3$ is H, F or Cl;
$R_4$ is H, $CH_3$, F or Cl;
$R_5$ is H, $CH_3$ or OH; or $OR_2$ and $R_5$ can together form a cyclic ketal;
$R_6$ and $R_7$, which can be the same or different, are each H, $C_1-C_8$ alkyl or

or $R_6$ and $R_7$, together with the nitrogen atom from which they both depend, can form a 5- or 6-membered N-heterocycle or a 5- or 6-membered N,O-heterocycle;
$R_8$ is $C_1-C_{20}$ alkyl, $C_2-C_{20}$ alkenyl, $C_3-C_7$ cycloalkyl, phenyl, ($C_1-C_4$ alkyl substituted)phenyl or $C_1-C_{20}$ alkyl-$C_6-C_{10}$ aryl;
X is OH or =O;
Y is $-(CH_2)_n-$ wherein n ranges from 1 to 8, $-(CH_2)_m-Z-(CH_2)_n-$ wherein both n and m range from 1 to 8, $C_3-C_7$ cycloalkyl or phenyl;
Z is O or S; and
the dotted line indicates the optional presence of a 1,2-double bond.

2. A compound as defined by claim 1 wherein $R_1$ is

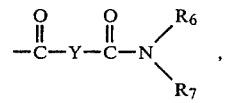

wherein Y, $R_6$ and $R_7$ are as defined in claim 1.

3. A compound as defined by claim 1 wherein $R_1$ is

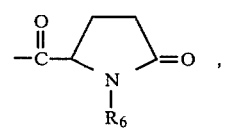

wherein $R_6$ is as defined in claim 1.

4. A compound as defined by claim 2 or 3 wherein $R_2$ is H.

5. A compound as defined by claim 2 or 3 wherein $R_2$ is $$-\overset{O}{\underset{\|}{C}}-R_8$$

wherein $R_8$ is $C_1-C_{20}$ alkyl.

6. A compound as defined by claim 1 wherein $R_2$ is $$-\overset{O}{\underset{\|}{C}}-Y-\overset{O}{\underset{\|}{C}}-N\overset{R_6}{\underset{R_7}{\diagdown}},$$

wherein Y, $R_6$ and $R_7$ are as defined in claim 1.

7. A compound as defined in claim 1 wherein $R_2$ is $$-\overset{O}{\underset{\|}{C}}\underset{\underset{R_6}{|}}{\diagdown N \diagup}=O,$$

wherein $R_6$ is as defined in claim 1.

8. A compound as defined by claim 6 or 7 wherein $R_1$ is H.

9. A compound as defined by claim 6 or 7 wherein $R_1$ is $$-\overset{O}{\underset{\|}{C}}-R_8$$

wherein $R_8$ is $C_1-C_{20}$ alkyl.

10. A compound as defined by claim 1, 2, 3, 6 or 7 wherein X is β-OH.

11. A compound as defined by claim 2 wherein Y is —(CH$_2$)$_\overline{n}$.

12. A compound as defined by claim 6 wherein Y is —(CH$_2$)$_\overline{n}$.

13. A compound as defined by claim 1 wherein $R_3$ is H.

14. A compound as defined by claim 1 wherein $R_3$ is F.

15. A compound as defined by claim 1 wherein $R_4$ is H.

16. A compound as defined by claim 1 wherein $R_4$ is F.

17. A compound as defined by claim 1, 2 or 3 wherein $R_5$ is H.

18. A compound as defined by claim 1, 2 or 3 wherein $R_5$ is CH$_3$.

19. A compound as defined by claim 1, 2 or 3 wherein $R_5$ is OH.

20. A compound as defined in claim 1, 2 or 3 wherein OR$_2$ and R$_5$ together form isopropylidenedioxy or benzylidenedioxy.

21. A compound as defined in claim 1, 2 or 3 wherein X is =O.

22. A compound as defined in claim 1 wherein $R_1$ is $$-\overset{O}{\underset{\|}{C}}-Y-\overset{O}{\underset{\|}{C}}-N\overset{R_6}{\underset{R_7}{\diagdown}} \text{ or } -\overset{O}{\underset{\|}{C}}\underset{\underset{R_6}{|}}{\diagdown N \diagup}=O$$

and the remainder of the structural variables are identical to those of a known anti-inflammatory steroid selected from the group consisting of cortisone, hydrocortisone, hydrocortisone 17-butyrate, hydrocortisone 17-valerate, triamcinolone, triamcinolone acetonide, prednisone, prednisolone, methyl prednisolone, paramethasone, meprednisone, fluocinolone acetonide, fluprednisolone, flumethasone, dexamethasone, desonide, chloroprednisone, betamethasone, amcinafide, amcinafal and flurandrenolone acetonide.

23. A compound as defined by claim 1, the same being 4-pregene-11β,17α-dihydroxy-21-(N,N-dimethylsuccinamyloxy)-3,20-dione.

24. A compound as defined by claim 1, the same being 4-pregnene-11β,17α-dihydroxy-21-(N,N-diethylsuccinamyloxy)-3,20-dione.

25. A compound as defined by claim 1, the same being 4-pregene-11β,17α-dihydroxy-21-(N,N-dipropylsucinamyloxy)-3,20-dione.

26. A compound as defined by claim 1, the same being 4-pregene-11β,17α-dihydroxy-21-(N,N-dibutylsuccinamyloxy)-3,20-dione.

27. A compound as defined by claim 1, the same being 4-pregene-11β,17α-dihydroxy-21-(N,N-dioctylsuccinamyloxy)-3,20-dione.

28. A compound as defined by claim 1, the same being 4-pregnene-11β,17α-dihydroxy-21-(N,N-tetramethylenesuccinamyloxy)-3,20-dione.

29. A compound as defined by claim 1, the same being 4-pregnene-11β,17α-dihydroxy-21-(N,N-pentamethylenesuccinamyloxy)-3,20-dione.

30. A compound as defined by claim 1, the same being 4-pregnene-11β,17α-dihydroxy-21-[N,N-(3'-oxapentamethylene)succinamyloxy]-3,20-dione.

31. A compound as defined in claim 1, the same being 4-pregnene-11β,17α-dihydroxy-21-[N,N-(N'-methyl-3'-azapentamethylene)succinamyloxy]-3,20-dione.

32. A compound as defined by claim 1, the same being 4-pregnene-11β,17α-dihydroxy-21-(N,N-dibenzylsuccinamyloxy)-3,20-dione.

33. A compound as defined by claim 1, the same being 4-pregnene-11β,17α-dihydroxy-21-(2'-oxopyrrolidin-5'-yl)carbonyloxy-3,20-dione.

34. A compound as defined by claim 1, the same being 4-pregnene-11β-hydroxy-17α-acetyloxy-21-(N,N-diethylsuccinamyloxy)-3,20-dione.

35. A compound as defined by claim 1, the same being 4-pregnene-11β-hydroxy-17α-butyryloxy-21-(N,N-diethylsuccinamyloxy)-3,20-dione.

36. A compound as defined by claim 1, the same being 4-pregnene-11β-hydroxy-17α-valeryloxy-21-(N,N-diethylsuccinamyloxy)-3,20-dione.

37. A compound as defined by claim 1, the same being 4-pregnene-11β,17α-dihydroxy-21-(N,N-diethylglutaramyloxy)-32,0-dione.

38. A compound as defined by claim 1, the same being 4-pregnene-11β,17α-dihydroxy-21-(N,N-diethyladipamyloxy)-3,20-dione.

39. A compound as defined by claim 1, the same being 4-pregnene-11β, 17α-dihydroxy-21-(N,N-diethylsebacamyloxy)-3,20-dione.

40. A compound as defined by claim 1, the same being 4-pregnene-11β,21-dihydroxy-17α-(N,N-dimethylsuccinamyloxy)-3,20-dione.

41. A compound as defined by claim 1, the same being 4-pregnene-11β,21-dihydroxy-17α-(N,N-diethylsuccinamyloxy)-3,20-dione.

42. A compound as defined by claim 1, the same being 4-pregnene-11β,21-dihydroxy-17α-(N,N-dipropylsuccinamyloxy)-3,20-dione.

43. A compound as defined by claim 1, the same being 4-pregnene-11β,21-dihydroxy-17α-(N,N-dibutylsuccinamyloxy)-3,20-dione.

44. A compound as defined by claim 1, the same being 4-pregnene-17α-hydroxy-21-(N,N-dioctylsuccinamyloxy)-3,11,20-trione.

45. A compound as defined by claim 1, the same being 4-pregnene-17α-hydroxy-21-(N,N-tetramethylenesuccinamyloxy)-3,11,20-trione.

46. A compound as defined by claim 1, the same being 4-pregnene-17α-hydroxy-21-(N,N-pentamethylenesuccinamyloxy)-3,11,20-trione.

47. A compound as defined by claim 1, the same being 1,4-pregnadiene-11β,17α-dihydroxy-21-[N,N-(3'-oxapentamethylene)succinamyloxy]-3,20-dione.

48. A compound as defined by claim 1, the same being 1,4-pregnadiene-11β,17α-dihydroxy-21-[N,N-(N'-methyl-3'-azapentamethylene)succinamyloxy]-3,20-dione.

49. A compound as defined by claim 1, the same being 1,4-pregnadiene-11β,17α-dihydroxy-21-(N,N-dibenzylsuccinamyloxy)-3,20-dione.

50. A compound as defined by claim 1, the same being 1,4-pregnadiene-17α-hydroxy-21-(2'-oxo-pyrrolidin-5'-yl)carbonyloxy-3,11,20-trione.

51. A compound as defined by claim 1, the same being 1,4-pregnadiene-17α-acetyloxy-21-(N,N-diethylsuccinamyloxy)-3,11,20-trione.

52. A compound as defined by claim 1, the same being 1,4-pregnadiene-17α-butyryloxy-21-(N,N-diethylsuccinamyloxy)-3,11,20-trione.

53. A compound as defined by claim 1, the same being 1,4-pregnadiene-9α-fluoro-11β,16α-dihydroxy-17α-valeryloxy-21-(N,N-diethylsuccinamyloxy)-3,20-dione.

54. A compound as defined by claim 1, the same being 1,4-pregnadiene-9α-fluoro-11β,16α,17α-trihydroxy-21-(N,N-diethylglutaramyloxy)-3,20-dione.

55. A compound as defined by claim 1, the same being 1,4-pregnadiene-9α-fluoro-11β,16α,17α-trihydroxy-21-(N,N-diethyladipamyloxy)-3,20-dione.

56. A compound as defined by claim 1, the same being 1,4-pregnadiene-9α-fluoro-11β-hydroxy-16α,17α-isopropylidenedioxy-21-(N,N-dimethylsuccinamyloxy)-3,20-dione.

57. A compound as defined by claim 1, the same being 1,4-pregnadiene-9α-fluoro-11β-hydroxy-16α,17α-isopropylidenedioxy-21-(N,N-diethylsuccinamyloxy)-3,20-dione.

58. A compound as defined by claim 1, the same being 1,4-pregnadiene-9α-fluoro-11β-hydroxy-16α,17α-isopropylidenedioxy-21-(N,N-dipropylsuccinamyloxy)-3,20-dione.

59. A compound as defined by claim 1, the same being 1,4-pregnadiene-9α-fluoro-11β,17α-dihydroxy-16α-methyl-21-(N,N-diethylsebacamyloxy)-3,20-dione.

60. A compound as defined by claim 1, the same being 1,4-pregnadiene-9α-fluoro-11β,21-dihydroxy-16α-methyl-17α-(N,N-dimethylsuccinamyloxy)-3,20-dione.

61. A compound as defined by claim 1, the same being 1,4-pregnadiene-9α-fluoro-11β,21-dihydroxy-16α-methyl-17α-(N,N-diethylsuccinamyloxy)-3,20-dione.

62. A compound as defined by claim 1, the same being 4-pregnene-9α-fluoro-11β,21-dihydroxy-17α-(N,N-dipropylsuccinamyloxy)-3,20-dione.

63. A compound as defined by claim 1, the same being 4-pregnene-9α-fluoro-11β,21-dihydroxy-17α-(N,N-dibutylsuccinamyloxy)-3,20-dione.

64. A compound as defined by claim 1, the same being 4-pregnene-9α-fluoro-11β,17α-dihydroxy-21-(N,N-dibutylsuccinamyloxy)-3,20-dione.

65. A compound as defined by claim 1, the same being 1,4-pregnadiene-11β-hydroxy-16α,17α-isopropylidenedioxy-21-(N,N-dioctylsuccinamyloxy)-3,20-dione.

66. A compound as defined by claim 1, the same being 1,4-pregnadiene-11β-hydroxy-16α,17α-isopropylidenedioxy-21-(N,N-tetramethylenesuccinamyloxy)-3,20-dione.

67. A compound as defined by claim 1, the same being 1,4-pregnadiene-11β-hydroxy-16α,17α-isopropylidenedioxy-21-(N,N-pentamethylenesuccinamyloxy)-3,20-dione.

68. A compound as defined by claim 1, the same being 1,4-pregnadiene-6α,9α-difluoro-16α-methyl-11β,17α-dihydroxy-21-[N,N-(3'-oxapentamethylene)-succinamyloxy]-3,20-dione.

69. A compound as defined by claim 1, the same being 1,4-pregnadiene-6α,9α-difluoro-16α-methyl-11β,17α-dihydroxy-21-[N,N-(N'-methyl-3'-azapentamethylene)-succinamyloxy]-3,20-dione.

70. A compound as defined by claim 1, the same being 1,4-pregnadiene-6α,9α-difluoro-16α-methyl-11α,17α-dihydroxy-21-N,N-dibenzylsuccinamyloxy)-3,20-dione.

71. A compound as defined by claim 1, the same being 1,4-pregnadiene-6α,9α-difluoro-11β-hydroxy-16α,17α-isopropylidenedioxy-21-(2'-oxopyrrolidin-5'-yl)carbonyloxy-3,20-dione.

72. A compound as defined by claim 1, the same being 1,4-pregnadiene-6α,9α-difluoro-11β-hydroxy-16α,17α-isopropylidenedioxy-21-(N,N-diethylglutaramyloxy)-3,20-dione.

73. A compound as defined by claim 1, the same being 1,4-pregnadiene-6α,9α-difluoro-11β-hydroxy-16α,17α-isopropylidenedioxy-21-(N,N-diethyladipamyloxy)-3,20-dione.

74. A compound as defined by claim 1, the same being 1,4-pregnadiene-9α-fluoro-11β-hydroxy-16α-methyl-17α-acetyloxy-21-(N,N-diethylsuccinamyloxy)-3,20-dione.

75. A compound as defined by claim 1, the same being 1,4-pregnadiene-9α-fluoro-11β-hydroxy-16α-methyl-17α-acetyloxy-21-(N,N-diethylsuccinamyloxy)-3,20-dione.

76. A compound as defined by claim 1, the same being 1,4-pregnadiene-9α-fluoro-11β-hydroxy-16α-methyl-17α-butyryloxy-21-(N,N-diethylsuccinamyloxy)-3,20-dione.

77. A compound as defined by claim 1, the same being 4-pregnene-11β,17α-dihydroxy-21-(N,N-diethyl-3'-oxaglutaramyloxy)-3,20-dione.

78. A compound as defined by claim 1, the same being 4-pregnene-11β-hydroxy-17α-butyryloxy-21-(2'-oxopyrrolidin-5'-yl)carbonyloxy-3,20-dione.

79. A compound as defined by claim 1, the same being 1,4-pregnadiene-27α-hydroxy-21-(N,N-diethylsuccinamyloxy)-3,11,20-trione.

80. A compound as defined by claim 1, the same being 1,4-pregnadiene-11β,17α-dihydroxy-9α-fluoro-16α-methyl-21-(N,N-diethylsuccinamyloxy)-3,20-dione.

81. A compound as defined by claim 1, the same being 4-pregnene-11β,21-dihydroxy-17α-(N,N-diethylsuccinamyloxy)-3,20-dione.

82. A compound as defined by claim 1, the same being 4-pregnene-11β,21-dihydroxy-17α-[N,N-(N'-methyl-3'-azapentamethylene)succinamyloxy]-3,20-dione.

83. A compound as defined by claim 1, the same being 4-pregnene-11β-hydroxy-17α,21-bis(N,N-diethylsuccinamyloxy)-3,20-dione.

84. A compound as defined by claim 1, the same being 4-pregnene-11β-hydroxy-21-(N,N-diethylsuccinamyloxy)-17α-[N,N-(N'-methyl-3'-azapentamethylene)-succinamyloxy]-3,20-dione.

85. A pharmaceutical composition of matter comprising an anti-inflammatory effective amount of a compound as defined by claim 1, and a pharmaceutically acceptable inert carrier.

86. A method for alleviating inflammation in or on a warm-blooded animal exhibiting an inflammatory response, which comprises administering thereto an anti-inflammatory effective amount of a compound as defined by claim 1.

* * * * *